United States Patent [19]

Gross

[11] 4,332,471

[45] Jun. 1, 1982

[54] CUVETTE WITH TUB-SHAPED BOTTOM FOR THE OPTICAL EXAMINATION OF LIQUIDS

[75] Inventor: Jürgen Gross, Hofheim am Taunus, Fed. Rep. of Germany

[73] Assignee: Hoechst Aktiengesellschaft, Frankfurt am Main, Fed. Rep. of Germany

[21] Appl. No.: 154,321

[22] Filed: May 29, 1980

[30] Foreign Application Priority Data

Jun. 2, 1979 [DE] Fed. Rep. of Germany ....... 2922697

[51] Int. Cl.³ ............................................ G01N 21/03
[52] U.S. Cl. ..................................................... 356/246
[58] Field of Search ................. 356/246, 440; 250/576

[56] References Cited

U.S. PATENT DOCUMENTS

| | | | |
|---|---|---|---|
| 4,021,124 | 5/1977 | Sarstedt | 250/576 X |
| 4,067,653 | 1/1978 | Fletcher et al. | 356/246 X |
| 4,251,159 | 2/1981 | White | 356/246 |

Primary Examiner—Vincent P. McGraw
Attorney, Agent, or Firm—Curtis, Morris & Safford

[57] ABSTRACT

A cuvette for holding a liquid to be examined optically has front, back, and side walls defining a rectangular cross section and a Y-shaped structure at the bottom thereof for holding the liquid. The Y-shaped structure extends between transparent front and back walls with an upper funnel mouth extending to the side walls, and a liquid holding portion formed of inner walls spaced between the side walls, and extending down to a rounded, tub-shaped bottom. The front walls are transparent and serve also to form the front and back of the liquid holding portion. The bottom preferably has a frustroconic surface to minimize the amount of liquid required for examination and to facilitate mixing of liquids added to the cuvette. The side walls extend below the tub-shaped bottom, and are joined to the front and back wall midway up the liquid holding portion by means of a rib, so that light is not scattered by the side walls and optical inhomogeneities are prevented.

6 Claims, 1 Drawing Figure

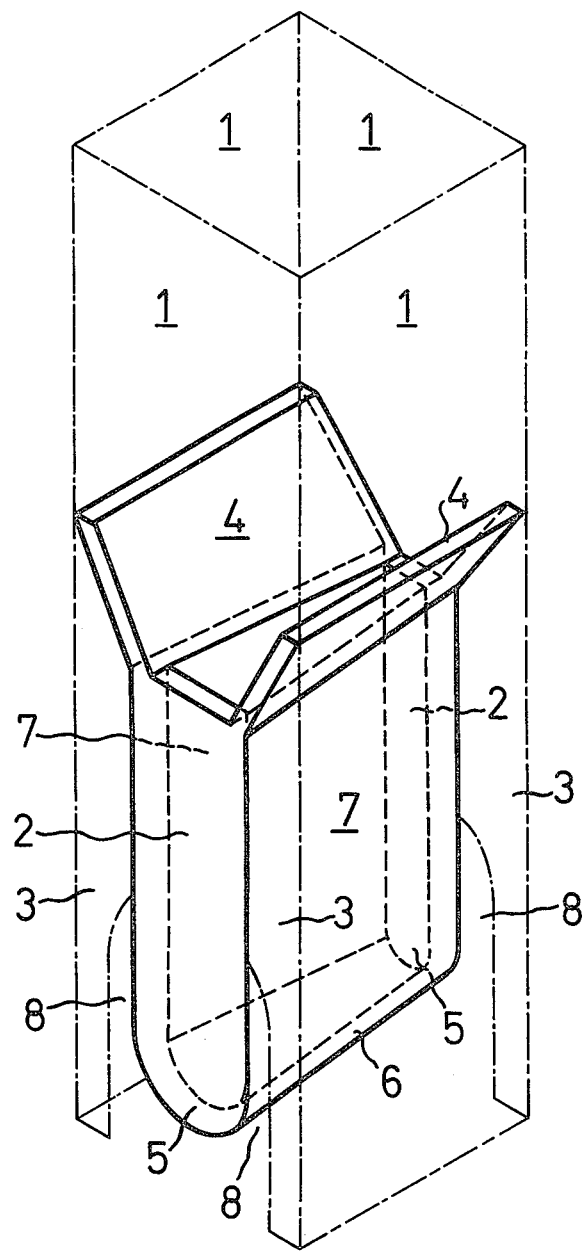

CUVETTE WITH TUB-SHAPED BOTTOM FOR THE OPTICAL EXAMINATION OF LIQUIDS

This invention is directed to a cuvette for the optical examination of liquids, especially for the examination thereof by means of laser light.

German Pat. No. 25 08 527 describes cuvettes made from plastic material or glass having a square-shaped cavity for liquids to be examined. However, when using laser light, only a frustoconic-shaped partial volume of this cavity is illuminated; the light ray being the axis of symmetry. Thus, a considerable part of the volume is unnecessary for optical measuring. Furthermore, in order to be fitted into the square holding device of the apparatus, known cuvettes are provided with ribs positioned parallel to the transilluminated walls. Because of this single-piece connection of ribs and wall, formation of optical inhomogeneities and/or corrugation in the transilluminated walls cannot be prevented. These optical inhomogeneities and/or corrugation adversely affect the optical measuring.

It is therefore the object of the invention to provide a cuvette of the above kind the cavity of which intended for containing the liquid to be examined is adapted to the course of the light rays used, and the ribs of which are shaped in such a manner that optical inhomogeneities and/or corrugation of the transilluminated walls is prevented in the penetration range of the rays.

In accordance with this invention, the above objects are achieved by a cuvette having transparent, parallel front and back walls and parallel side walls arranged so that the top of the cuvette has a rectangular cross section. A liquid-holding portion is formed of two inner walls within the side walls and extending between the front and back walls. The bottoms of the front and back walls end in semicircular surfaces, and a liquid-holding portion has a curved surface joining the inner walls and extending between the semicircular front and back surfaces. The side walls extend below the position of the bottom of the liquid-holding portion, and are joined thereto by ribs coplanar with the front wall and back wall, respectively, midway up the inner walls. These ribs define recesses for preventing scattering of light rays to the side walls. Funnel plates extend from the tops of the inner walls to the respective side walls.

In a preferred embodiment, the front and back semicircular surfaces have different diameters, and the bottom has generally the shape of half a conic frustum.

The above and other objects, features, and advantages of this invention can be better understood from the ensuing description of a preferred embodiment, considered with the accompanying sole drawing FIGURE.

The FIGURE is an isometric view of one possible embodiment of the cuvette of this invention.

A cuvette in accordance with the invention made from plastic material or glass and intended for the optical examination of small amounts of liquid has a tub-shaped bottom 6 the front surfaces 5 of which have a semicircular cross-section, and four walls emanating from the bottom, two of which being opposite, transparent front and back walls 2, 2 parallel to each other, the outer faces thereof having a defined distance from each other, while two inner side walls 7 are spaced at a smaller distance from each other in order to reduce the amount of liquid to the minimum required for examination. The cavity so shaped and intended for containing the liquid to be examined is surrounded by a housing forming a shaft of square cross-section by means of outer side walls 1 and front and back walls 1 coplanar with the front and back walls 2, and connected to a cavity by sloping funnel formed by the walls 4. The outer sidewalls extend below the bottom 6, and are joined to the front and back walls 2 by means of ribs 3 complanar with the respective walls and defining recesses 8 extending well above the bottom 6. In a special embodiment of the invention, the tub-like bottom has the shape of a halved conic frustum.

At identical optical properties, a cuvette having a bottom so shaped has a volume reduced by up to about 40% as compared to known cuvettes. Moreover, such a bottom enhances intermixing of liquids introduced one after the other, for example in the case of determining the concentration of antigens in solution by precipitation with the aid of the corresponding antibody.

The optical quality of the cuvettes of the invention is further improved in the shape of the transparent front surfaces 5 of the bottom 6 and by the recesses 8 defined by the ribs 3. Because, in this case, two surfaces only are adjacent to each other in this section of the cuvette, the disturbing formation of optical inhomogeneities and/or corrugation on the transparent front faces 5 and part of the front walls 2 is prevented.

What is claimed is:

1. A cuvette for the optical examination of small amounts of liquids comprising
    front and back parallel flat transparent walls whose outer surfaces are a defined distance from one another;
    two side walls separated by a distance less than said defined distance and extending between said front and back walls, and ending in a bottom joining the two side walls; and
    ribs coplanar with outer faces of the front and back walls, extending outwardly from said inner walls, and being joined thereto above said bottom to define respective recesses extending above the bottom;
    wherein said front and back walls end in semicircular surfaces at said bottom, and said bottom includes a surface of rotation joining said front and back semicircular surfaces so that said bottom is tub shaped.

2. A cuvette for the optical examination of small amounts of liquid as recited in claim 1, wherein said front and back semicircular surfaces have different cross sections, and said surface of rotation is substantially half a conic frustum.

3. A cuvette for the optical examination of small amounts of liquid as recited in claim 1, further comprising a pair of parallel outer side walls forming, with said front and back walls and the associated ribs, a cuvette frame of rectangular cross section.

4. A cuvette for the optical examination of small amounts of liquid as recited in claim 3, wherein said outer side walls extend below the extent of said bottom.

5. A cuvette for the optical examination of small amounts of liquid as recited in claim 3, wherein said cuvette frame extends above the first-mentioned side walls, and the cuvette further comprises funnel walls respectively slopingly extending from said outer side walls to said first-mentioned side walls.

6. A cuvette for the optical examination of small amounts of liquid as recited in claim 1, wherein said front and back walls each have a substantially rectangular portion having a width substantially the same as the diameter of said semicircular surfaces so that the front and back end walls have a generally U-shaped perimeter.

* * * * *